United States Patent

Gross et al.

Patent Number: 5,641,509
Date of Patent: Jun. 24, 1997

[54] PREPARATION FOR TOPICAL USE

[75] Inventors: Udo Gross, Berlin; Joachim Röding, Wiesbaden, both of Germany; Klaus Stanzl, White Plains, N.Y.; Leonhard Zastrow, Monaco, Monaco

[73] Assignee: Lancaster Group AG, Ludwigshafen, Germany

[21] Appl. No.: 640,116

[22] Filed: Apr. 30, 1996

Related U.S. Application Data

[63] Continuation of Ser. No. 360,842, filed as PCT/DE93/00573, Jun. 24, 1993 published as WO94/00097, Jan. 6, 1994, abandoned.

[30] Foreign Application Priority Data

Jun. 26, 1992 [DE] Germany ............... 42 21 269.3

[51] Int. Cl.$^6$ .................. A61K 9/127; A61K 7/00
[52] U.S. Cl. .................. 424/450; 424/63; 424/401; 264/41; 264/43; 514/944; 514/969
[58] Field of Search .................. 426/450, 63, 401, 426/43–45; 264/4.1, 4.3; 514/944, 969

[56] References Cited

U.S. PATENT DOCUMENTS 5,061,484 10/1991 Heldebrant .
5,219,538 6/1993 Henderson .................. 428/402.2
5,286,979 2/1994 Berliner .................. 250/515.1

FOREIGN PATENT DOCUMENTS

| 0069307 | 1/1983 | European Pat. Off. . |
| 0386680 | 9/1990 | European Pat. Off. . |
| 32 42 385 | 2/1987 | Germany . |
| 41 27 442 | 2/1993 | Germany . |
| 8900848 | 2/1989 | WIPO . |
| 89/08459 | 9/1989 | WIPO . |
| 91/00110 | 1/1991 | WIPO . |

OTHER PUBLICATIONS

Lautenschlager in Cosmetics & Toiletries 105, May 1990.

*Primary Examiner*—Gollamudi S. Kishore
*Attorney, Agent, or Firm*—Collard & Roe, P.C.

[57] ABSTRACT

The invention relates to a preparation for topical use, having light protection properties and in a special application form. In the known light protection agents containing the naturally occurring active compound melanin, the problem is inadequate transport of the melanin to its site of action. According to the invention, this problem is solved by a preparation for topical use which is characterised in that it contains melanin, dissolved or dispersed in one or more fluorocarbons, which are present as asymmetric lamellar phospholipid aggregates in an aqueous system together with a phospholipid, with a particle size of the aggregates in the range from 200 to 3000 nm.

21 Claims, 2 Drawing Sheets

PREPARATION FOR TOPICAL USE

This is a continuation of application Ser. No. 08,360,842 filed on Dec. 22, 1994, now abandoned. International Application PCT/DE93/00573 filed on 24 Jun. 1993 published as WO94/00097, Jan. 6, 1994 and which designated the U.S.

The invention relates to a cosmetic or dermatological composition having light protection properties in a special application form, in which fluorocarbon-containing asymmetric lamellar phospholipid aggregates function as carriers of melanin.

It is known that short-wave UV light (UV/A, UV/B, UV/C, wavelength ranges from 400 to 200 nm) can have a damaging effect on the skin and is a significant factor for premature skin aging. In extreme form, the action can consist in a cytogenetic change in individual skin cells and lead to the formation of skin carcinomas (melanomas). These hazards have continuously increased due to environmentally related factors (ozone hole) with an increased UV burden. In order to overcome this fact, it is customary, by means of special cosmetics and dermatological agents, to protect the exposed skin tissue by the use of special UV light protection filters. The active compound of these compositions is based on the following principles:

1. Absorption of UV light by the use of UV-active organic compounds
2. Scattering of UV light by finely dispersed titanium dioxide or other micropigments The efficacy of these systems, which can be detected simply by recording their UV absorption maxima in the wavelength range 250–400 nm or by scattering curves, is evident. The problem, however, is the biological acceptability of the substances, in particular the possible chemical substance alterations under the influence of energy-rich radiation.

A further critical point is the depth of penetration of the UV filter into the skin when it is used as a constituent of a cosmetic or dermatological agent. The suitable site of action is the region between the horny layer and basal layer. In order to meet these demands, testing for one year is necessary, as has been previously prescribed for pharmacological active compounds. Accordingly to their intended use and their individual efficacy, the UV filters are applied topically in a suitable medium in a wide concentration range between 1 and 10%.

Thus, e.g., DE-A-3242385 (Zabotto) describes a cosmetic composition which, in addition to other active compounds, contains 1.5% Parsol Ultra (Givaudan) for the reduction of skin aging due to the action of light.

Melanin, which also occurs in human and animal cells, the melanocytes, is known as a natural light protection active compound in higher organisms. Melanin is a brown to black-coloured polymeric pigment of the vertebrates, which is formed, inter alia, from the amino acid tyrosine and pigments both skin, hair and iris. The melanin formed in the melanocytes of the skin migrates into the basal layer of the epidermis and there releases the pigment into the epidermal cells. Since melanin, as a polymeric substance, hardly dissolves, the previous attempts to bring this substance to its site of action by means of topical applications are to be regarded as not thoroughly successful.

The invention has set the object of making possible topical use of melanin at its site of action.

According to the invention, a preparation for topical use having light protection properties is characterised in that it contains melanin which is dissolved or dispersed in one or more lipophilic fluorocarbons which are present as asymmetric lamellar phospholipid aggregates in an aqueous system together with a phospholipid, with a particle size of the aggregates gates in the range from 200 to 3000 nm.

The naturally obtained (e.g. from Sepia officinalis) or synthetically produced (oxidation of tyrosine, e.g. with $H_2O_2$) melanin is present, dissolved or suspended by the fluorocarbon, encapsulated in the core of the asymmetric lamellar phospholipid aggregates. The structural arrangement in the lamellar aggregates is fundamentally different from that of aqueous liposomes (vesicles). The hydrophobic nature of the fluorocarbon calls for a reversal in the polarity of the phospholipid molecule such that the lipophilic fatty acid radicals interact with the fluorocarbon in the core of the aggregate gate by dispersive forces. In this arrangement, further phospholipid bilayer films are constructed to give asymmetric metric lamellar globular aggregates according to specified conditions.

The novel asymmetric structure was confirmed by $^{31}P$-NMR investigations and spectroscopic investigations. The exceptional stability of the aggregates results from their lamellar structure and from the corresponding surface charge.

A plurality of fluorocarbons can be employed, e.g. aliphatic straight-chain and branched fluoroalkanes, mono- or bicyclic and optionally fluoroalkyl-substituted fluorocycloalkanes, perfluorinated aliphatic or bicyclic amines, bis(perfluoroalkyl)ethenes, perfluoropolyethers and mixtures thereof. Particularly preferred fluorocarbons are those such as perfluorodecalin, F-butyltetra-hydrofuran, perfluorotributylamine, perfluorooctyl bromide, bis-fluoro (butyl)ethene or bis-fluoro(hexyl)-ethene or $C_6$–$C_9$-perfluoroalkanes. The amount of fluoro-carbons here is in the range from 20 to 100% w/v, preferably in the range from 40 to 100%. A particularly preferred range is that from 70 to 100% w/v.

It was possible to determine the dependence of the penetration rate and the depth of penetration on the particle size of the aggregates experimentally by separate investigations using labelled encapsulated fluorocarbons. According to these experiments, smaller particles migrate more rapidly and more deeply into the skin tissue than larger particles. The choice of fluorocarbons or their mixtures according to their lipid solubility (represented by their critical solubility temperature CST in n-hexane) allows, as a further important criterion, the regulation of the residence time in the tissue. While, e.g. perfluorotributylamine (F-TBA, CST 59° C.) having a high CST value and poor lipid solubility has a relatively high residence time, in contrast to this perfluorodecalin (PFD, CST 22° C.) but also F-butyltetra-hydrofuran, F-hexane and others are released correspondingly more rapidly from the tissue. With the aid of fluorocarbon mixtures, systems with desired CST values, i.e. lipid and membrane solubilities, can be prepared specifically with respect to the intended use.

The content of the fluorocarbons in the lamellar. aggregates can vary between 1 and 100% w/v according to the intended use. Suitable fluorocarbons are in particular:

aliphatic straight-chain and branched alkanes having 6 to 12 carbon atoms, e.g. perfluorohexane, perfluorooctane, perfluorononane;

mono- or bicyclic cycloalkanes, which are optionally F-alkyl-substituted, e.g. perfluoromethylcyclohexane, perfluorodecalin;

aliphatic tertiary amines, N-containing polycycles, e.g. perfluorotripopylamine [sic], perfluorotributylamine, F-cyclohexylmethylmorpholine;

perfluoroethers, such as aliphatic ethers, F-alkylfurans, bicyclic and substituted bicyclic ethers having two or three oxygen atoms in the molecule, e.g. perfluorodihexyl ether, perfluorobutyltetrahydrofuran, perfluoropoly-ethers;

perfluoroalkyl halides, e.g. perfluorooctyl bromide, perfluorohexyl bromide, perfluorooctyl chloride; Bis-F (alkyl)ethenes, e.g. bis-F(butyl)ethene, bis-F(hexyl) ethene.

The term "fluorocarbons" used here is understood as meaning perfluorinated or highly fluorinated carbon compounds or mixtures which are able to transport gases such as $O_2$ and $CO_2$. Partially fluorinated hydrocarbon compounds within the context of this invention are those in which most of the hydrogen atoms are replaced by fluorine atoms, e.g. the bis-F(alkyl)ethenes which, as far as can be detected, are chemically and biologically inert and thus non-toxic. This is usually achieved when approximately up to 90% of the hydrogen atoms are replaced by fluorine atoms. Preferred fluorocarbons within the context of the present invention are those in which at least 955 of the hydrogen atoms are replaced, more preferably 98% and most preferably 100%.

Suitable phospholipids are naturally occurring phospholipids such as soya or egg lecithin, and also lecithins (phospholipids) which can be prepared synthetically and which overall are known as being skin-compatible and good for the skin. Because of the advantageous action on the stability of the asymmetric lamellar aggregates, phospholipid mixtures having a content from 10 to 99%, preferably 30 to 99%, in particular 60 to 90% of phosphatidylcholine in addition to other naturally occurring accompanying products are preferably used. The phospholipid content in the topical formulation varies between 0.5 and 20%, preferably 10 to 20%.

The particle sizes of the aggregates, and the phospholipids are selected such that a penetration into deeper layers of the skin, e.g. into the epidermis or the dermal region does not take place and the light protection filter according to the invention thus reaches its site of action after it has penetrated the horny layer. The particle sizes are in the range from 200 to 3000 nm, preferably in the range from 250 to 1000 nm.

The invention also relates to a process for the production of preparations for topical use, which is characterised in that melanin is dissolved or dispersed in one or more fluorocarbons and this dispersion is converted by homogenisation with a phospholipid in an aqueous system into asymmetric lamellar phospholipid aggregates containing the fluorocarbons and melanin, having particle sizes between 200 and 3000 nm.

The solubility of the polymeric melanin can be increased by addition of lipophilic substances to the fluorocarbon as solubilisers. Suitable lipophilic substances are native oils, triglycerides or aliphatic alkanes, selected from the group consisting of olive oil, soya bean oil, sunflower oil, pentane, heptane, nonane, decane or mixtures thereof.

The homogenisation can be effected by customary processes, e.g. using a high-speed stirrer (12,000 to 15,000 rpm), by ultrasound or by means of pressure homogenisation such that the particle size is ensured.

BRIEF DESCRIPTION OF THE DRAWINGS

The invention will be illustrated in greater detail below by means of examples. In the associated drawings

Figure 1:
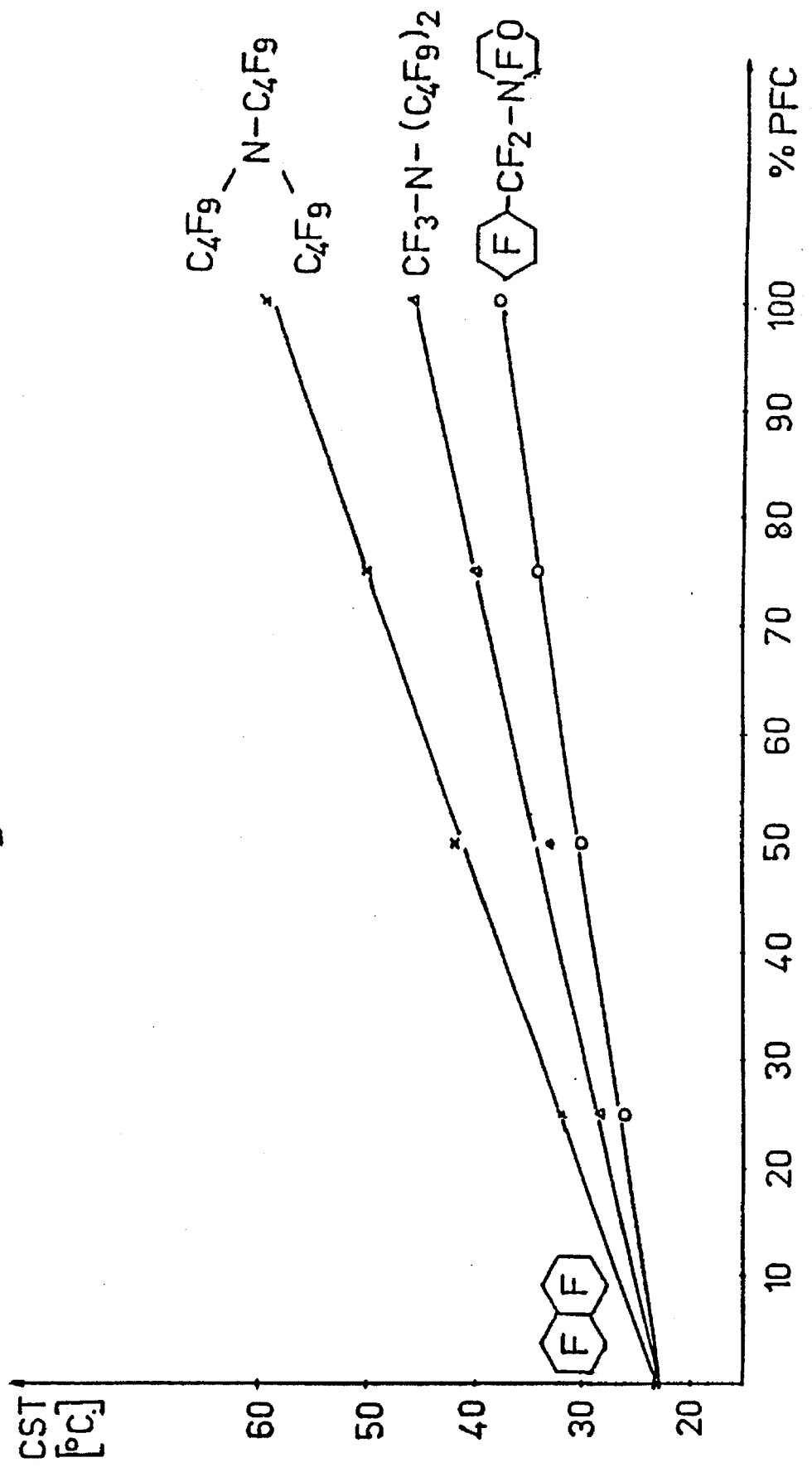
FIG. 1 is a diagram of the critical solubility temperatures (CST) of perfluorocarbon mixtures in n-hexane using perfluorodecalin as a starting point
Figure 2:
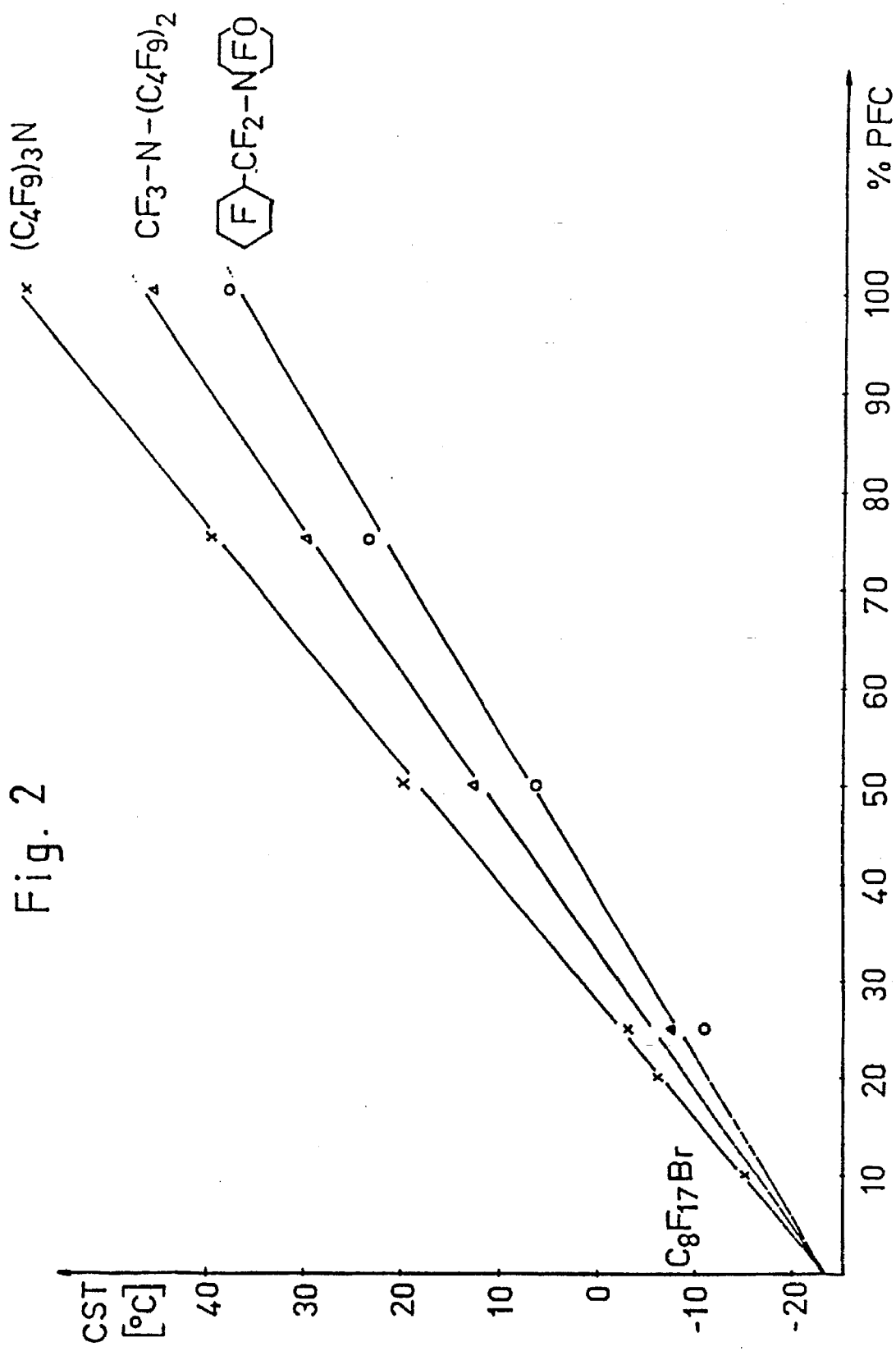
FIG. 2 is a diagram of the critical solubility temperatures of perfluorocarbon mixtures in n-hexane using F-octylbromide as a starting point.

Some selected fluorocarbons and their $O_2$ solubility, their vapour pressure and their critical solubility temperature are shown in Table 1. Starting from these values, the desired characteristics for the penetration of the skin with the aid of the composition according to the invention can be selected for mixtures of fluorocarbons.

TABLE 1

| Fluorocarbon | $O_2$ solubility [m] [sic] of $O_2$/100 ml of Fc] | Vapour Pressure $P_{37°C.}$ [mm Hg] | CST [°C.] |
| --- | --- | --- | --- |
| Perfluorooctyl bromide | 50 | 14 | −24.5 |
| Perfluorodecalin | 40 | 12.5 | 22 |
| bis-F(butyl)ethene | 50 | 12.6 | 22.5 |
| F-cyclohexylmethyl-morpholine | 42 | 4 | 38.5 |
| F-tripropylamine | 45 | 18.5 | 43 |
| F-dihexyl ether | 45 | 2 | 59 |
| F-tributylamine | 40 | 1 | 59 |
| Perfluorodecalin-F-tributylamine 1:1 | 40 | 7 | 42 |
| Perfluorobutyl-tetrahydrofuran | 52 | 51 | 29 |
| F-methylcyclohexane | 57 | 180 | 8.2 |
| F-hexane | 58 | 414 | 20 |

EXAMPLE 1

A 10% strength aqueous phospholipid solution of soya lecithin and containing 40% phosphatidylcholine was mixed with cooling in an ultrasonic disintegrator with a fluorocarbon mixture composed of perfluorodecalin (90%) and F-dibutylmethylamine (10%) and melanin. The asymmetric lamellar phospholipid aggregates obtained in this process had a mean particle size of approximately 240 nm and contained the melanin.

The aggregates prepared in this manner were incorporated into the following processing forms of light protection agents according to customary processes.

EXAMPLE 2

Emulsion (body lotion)

| Polyacrylic acid | 0.30% |
| --- | --- |
| TEA | 0.30% |
| p-Methylhydroxybenzoate | 0.20% |
| p-Propylhydroxybenzoate | 0.10% |
| Imidazolidinylurea | 0.20% |
| Na EDTA | 0.06% |
| Cetyl/stearyl alcohol | 1.00% |
| Stearic acid | 1.00% |
| Isopropyl myristate/palmitate | 3.00% |
| Liquid paraffin | 4.00% |
| Jojoba oil | 2.00% |
| Melanin/phospholipid aggregates | 10.00% |
| Perfume oil | 1.00% |
| Demineralised water | q.s. |

EXAMPLE 6

[sic]Emulsion (cream)

| Polyacrylic acid | 0.30% |
| --- | --- |
| Propylene glycol | 5.00% |
| TEA | 0.30% |
| Emulsifier 1 | 6.00% |
| Emulsifier 2 | 4.50% |

-continued

| | |
|---|---|
| Aloe vera | 2.00% |
| Rice husk oil | 1.50% |
| Cetyl/stearyl alcohol | 1.00% |
| Jojoba oil | 1.50% |
| p-Methylhydroxybenzoate | 0.20% |
| p-Propylhydroxybenzoate | 0.10% |
| Imidazolidinylurea | 0.20% |
| Melanin/phospholipid aggregates | 20.00% |
| Perfume oil | 1.00% |
| Demineralised water | q.s. |

EXAMPLE 4

Lotion

| | |
|---|---|
| Emulsifier system consisting of water, stabilisers, polyglycerol esters, polyoxyethylene esters, isopropyl palmitate | 34.00% |
| Glycerol | 5.00% |
| MgSO$_4$.7H$_2$O | 0.50% |
| Melanin/phospholipid aggregates | 6.00% |
| p-Methylhydroxybenzoate | 0.20% |
| p-Propylhydroxybenzoate | 0.10% |
| Imidazolidinylurea | 0.30% |
| Perfume oil | 1.00% |
| Demineralised water | q.s. |

EXAMPLE 5

Eyeshadow, compressed with light protection factor

| | |
|---|---|
| Talc | 40.00% |
| Mg carbonate | 1.50% |
| Mg stearate | 2.50% |
| Kaolin | 2.20% |
| Colorants | 15.80% |
| Pearl lustre pigments | 21.50% |
| Perfume oil | 1.50% |
| Silk protein | 5.00% |
| Emulsion as processing means Emulsifier | 4.50% |
| Silicone oil, volatile | 2.50% |
| Melanin/phospholipid aggregates | 4.50% |
| Preservative | 0.30% |
| Demineralised water | q.s. |

We claim:

1. Preparation for topical use, consisting of melanin, dissolved or dispersed in one or more fluorocarbons; said fluorocarbons present as asymmetric lamellar phospholipid aggregates in an aqueous system together with a phospholipid, with a particle size of the aggregates in the range from 200 to 3000 nm;

said asymmetric lamellar phospholid aggregates comprising a central core of fluorocarbons surrounded by at least three layers of phospholipid molecules wherein the layer adjacent to said central core has the lipophilic moiety of the phospholipid interact with the fluorocarbon; and wherein the phospholipid has a phosphatidylcholine content of from 30% to 99% by weight.

2. Preparation according to claim 1, wherein the amount of fluorocarbon is in the range of from 1% to 100% w/v.

3. Preparation according to claim 1, wherein the fluorocarbon is selected from the group consisting of aliphatic straight-chain fluoroalkanes, aliphatic branched fluoroalkanes, monocyclic fluorocycloalkanes, monocyclic fluoroalkyl-substituted fluorocycloalkanes, bicyclic fluorocycloalkanes, bicyclic fluoroalkylsubstituted fluorocycloalkanes, perfluorinated fluorinated aliphatic amines, per-fluorinated bicyclic amines, bis(perfluoroalkyl) ethenes, perfluoropolyethers and mixtures thereof.

4. Preparation according to claim 3, wherein the fluorocarbon is selected from the group consisting of perfluorodecalin, F-butyltetrahydrofuran, perfluorotributylamine, perfluorooctyl bromide, bis-fluoro(butyl)ethene and $C_6$–$C_9$- perfluoroalkanes.

5. Preparation according to claim 1, wherein the amount of fluorocarbon is in the range from 20% to 100% weight/volume.

6. Preparation according to claim 1, wherein the amount of fluorocarbon is in the range from 40% to 100% weight/volume.

7. Preparation according to claim 1, wherein the amount of fluorocarbon is in the range from 70% to 100% weight/volume.

8. Preparation according to claim 1, wherein one or more fluorocarbons have a critical solubility temperature below 50° C.

9. Preparation according to claim 1, wherein one or more fluorocarbons have a critical solubility temperature below 30° C.

10. Preparation according to claim 1, wherein the phospholipids are selected from the group consisting of natural phospholipids, synthetic phospholipids, and the mixtures thereof.

11. Preparation according to claim 1, wherein phosphatidylcholine is present in the amount from 10% to 99% by weight.

12. Preparation according to claim 1, wherein phosphatidylcholine is present in the amount from 30% to 99% by weight.

13. Preparation according to claim 1, wherein phosphatidylcholine is present in an amount from 70% to 90% by weight.

14. Preparation according to claim 1, wherein, in addition to phosphatidylcholine, lysolecithins are present in the concentration range from 1% to 10% by weight.

15. Preparation according to claim 1, wherein, in addition to melanin and fluorocarbon, a solubilizer, selected from group consisting of olive oil, soya bean oil, sunflower oil, triglycerides, pentane, heptane, nonane, decane, and the mixtures thereof, is present.

16. Process for the production of preparations for topical use, consisting of the steps of dissolving or dispersing melanin in one or more fluorocarbons to produce a solution or a dispersion;

converting this solution or dispersion by homogenization with a phospholipid in an aqueous system into asymmetric lamellar phospholipid aggregates containing the fluorocarbon and melanin, having particle sizes between 200 and 3000 nm; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon; and wherein the phospholipid has a phosphatidylcholine content of from 30% to 99% by weight.

17. Process according to claim 16, wherein a solubilizer, selected from the group consisting of olive oil, soya bean oil, sunflower oil, triglycerides, pentane, heptane, nonane, decane, and mixtures thereof is added to melanin and the fluorocarbon.

18. In a method for introducing melanin into the skin region above the epidermis, the improvement which consists of utilizing asymmetric lamellar phospholipid aggregates consisting of a phospholipid and one or more fluorocarbons containing melanin dissolved or dispersed therein, the particle size of the aggregates being in the range from 200 to 3000 nm, for said introducing; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon; and wherein the phospholipid has a phosphatidylcholine content of from 30% to 99% by weight.

19. The method according to claim 1, wherein there is a phosphatidylcholine content of the phospholipid from 70% to 90% by weight.

20. The method according to claim 16, wherein there is a phosphatidylcholine content of the phospholipid from 70% to 90% by weight.

21. The method according to claim 18, wherein there is a phosphatidylcholine content of the phospholipid from 70% to 90% by weight.

* * * * *